United States Patent [19]
Lin et al.

[11] Patent Number: 5,482,828
[45] Date of Patent: * Jan. 9, 1996

[54] SYNTHETIC MEDIA COMPOSITIONS AND METHODS FOR INACTIVATING BACTERIA AND VIRUSES IN BLOOD PREPARATIONS WITH 8-METHOXYPSORALEN

[75] Inventors: Lily Lin; Lawrence Corash, both of Berkeley; Stephen Isaacs, Orinda; George Cimino, Richmond, all of Calif.

[73] Assignee: Steritech, Inc., Concord, Calif.

[*] Notice: The portion of the term of this patent subsequent to Feb. 22, 2011, has been disclaimed.

[21] Appl. No.: 207,798

[22] Filed: Mar. 7, 1994

Related U.S. Application Data

[63] Continuation of Ser. No. 926,477, Aug. 7, 1992, abandoned, which is a continuation of Ser. No. 844,790, Mar. 2, 1992, Pat. No. 5,288,605.

[51] Int. Cl.$^6$ .............................. A01N 1/02; A61K 41/00; A61M 37/00
[52] U.S. Cl. .............................. 435/2; 424/93.72; 604/4; 604/20
[58] Field of Search .............................. 435/2; 424/90, 424/530; 604/4, 20

[56] References Cited

U.S. PATENT DOCUMENTS

| | | | |
|---|---|---|---|
| Re. 32,874 | 2/1989 | Rock et al. | 424/101 |
| 2,786,014 | 3/1957 | Tullis | 167/78 |
| 3,629,071 | 12/1971 | Sekhar | 195/1.8 |
| 3,729,947 | 5/1973 | Higuchi | 62/60 |
| 3,735,005 | 5/1973 | Shio et al. | 424/101 |
| 3,874,384 | 4/1975 | Deindoerfer et al. | 128/272 |
| 4,124,598 | 11/1978 | Hearst et al. | 260/343.21 |
| 4,152,208 | 5/1979 | Guirgis | 195/1.8 |
| 4,169,204 | 9/1979 | Hearst et al. | 546/270 |
| 4,196,281 | 4/1980 | Hearst et al. | 536/28 |
| 4,321,919 | 3/1982 | Edelson | 128/214 |
| 4,344,936 | 8/1982 | Soslau | 424/101 |
| 4,390,619 | 6/1983 | Harmening-Pittiglio | 435/2 |
| 4,447,415 | 5/1984 | Rock et al. | 424/101 |
| 4,639,373 | 1/1987 | Babior | 424/101 |
| 4,695,460 | 9/1987 | Holme | 424/101 |
| 4,704,352 | 11/1987 | Miripol et al. | 435/2 |
| 4,727,027 | 2/1988 | Wiesehahn et al. | 435/173 |
| 4,748,120 | 5/1988 | Wiesehahn | 435/173 |
| 4,828,976 | 5/1989 | Murphy | 435/2 |
| 4,878,891 | 11/1989 | Judy | 604/5 |
| 4,925,665 | 5/1990 | Murphy | 424/532 |
| 4,944,920 | 7/1990 | Rubinstein | 422/37 |
| 4,960,408 | 10/1990 | Klainer | 604/4 |
| 4,992,363 | 2/1991 | Murphy | 435/2 |
| 4,997,577 | 3/1991 | Stewart | 210/767 |
| 5,011,695 | 4/1991 | Dichtelmuller et al. | 424/529 |
| 5,288,605 | 2/1994 | Lin | 435/2 |

OTHER PUBLICATIONS

B. J. Grossman et al., Transfusion 31:500 (1991).
B. A. Myhre, JAMA 244:1333 (1980).
J. M. Heal et al., Transfusion 27:2 (1987).
D. H. Buchholz, et al., Transfusion 13:268 (1973).
D. H. Buchholz, et al., New Eng. J. Med. 285:429 (1971).
J. F. Morrow et al., JAMA 266:555 (1991).
G. D. Cimino et al., Ann. Rev. Biochem. 54:1151 (1985).
Hearst et al., Quart. Rev. Biophys. 17:1 (1984).
S. T. Isaacs et al., Biochemistry 16:1058 (1977).
S. T. Isaacs et al., Trends in Photobiology (Plenum) p. 279 94 (1982).

(List continued on next page.)

Primary Examiner—Michael G. Wityshyn
Assistant Examiner—Ralph Gitomer
Attorney, Agent, or Firm—Peter G. Carroll; Kathryn P. Wilke

[57] ABSTRACT

Methods and compositions are described for treating contaminants in material intended for in vivo use, and in particular blood and blood products for human use. Compositions of synthetic media are described which optimize conditions for inactivation of contaminants in blood cell preparations, using 8-methoxypsoralen, prior to long term storage and transfusion.

20 Claims, 11 Drawing Sheets

OTHER PUBLICATIONS

J. Tessman et al., Biochem. 24:1669 (1985).
H. J. Alter et al., The Lancet (ii:1446) (1988).
L. Lin et al., Blood 74:517 (1989).
Hyde and Hearst, Biochemistry 17:1251 (1978).
Thompson et al., J. Mol. Biol. 147:417 (1981).
Thompson et al., Biochemistry 21:1363 (1982).
Infect. Control 5:343 (1984).
M. Artuc et al., Brit. J. Derm. 101:669 (1979).
M. J. Metzelaar, Studies on the Expression of Activation–Markers on Human Platelets (Thesis 1991).
Goddard, D., Jacobs, S. I., Manohitharajah, S. M., "The Bacteriological Screening of Platelet Concentrates Stored at 22 C," Transfusion 13:103 (1973).
Meek, E. et al., "Bacterial Proliferation in Human Platelet Concentrates Stored in Plasma or Artificial Medium," P.F.1.90 (ISBT) (1988).
Cordle, D., Koepke, J. A., and Koontz, F. P., "The Sterility of Platelet and Granulocyte Concentrates Collected by Discontinuous Flow Centrifugation," Transfusion 30:105 (1980).
Dodd, R. Y. et al., "Inactivation of Viruses in Platelet Suspensions that Retain Their In Vitro Characteristics: Comparison of Psoralen–ultraviolet A and Merocyanine 540 Visible Light Methods," Transfusion 31:483 (1991).
Kasha, M., "Transmission Filters for the Ultraviolet," Jour. Optical Soc. Amer. 38:929 (1948).
Ben–Hur, E., et al., "Measurement of DNA Crosslinks by S1 Nuclease: Induction and Repair in Psoralen–Plus–360 nm Light Treated *Escherichia coli*," Photochemistry and Photobiology 29:921 (1979).
Bordin, F. et al., "DNA Repair and Recovery in *Escherichia coli* after Psoralen and Angelicin Photosensitization," Biochimica et Biophysica Acta 447:249 (1976).
Bridges, B. A., "8–Methoxypsoralen and Radiation Damage in Bacteria," Int. Jour. Radiation Bio. 20:185 (date not available).
Fujita, H. and Kakishima, H., "Photobiological Activities of 5–alkoxypsoralens with Respect to the Action on *Escherichia coli*," Photochemistry and Photobiology 43:221 (1986).
Hass, B. S. and Webb, R. B., "8–Methoxypsoralen Effects on Survival and Repair of *Escherichia coli* after Ultraviolet Irradiation: Action Spectra," Radiation Research 80:170 (1979).
Belogurov, A. A. and Zavil'gel'skii, G. B. "Mechanism of the Inactivation Action of the Photosensitizer 8–Methoxypsoralen on Bacteria and Bacteriophages," Sovgenet 14:219 (1978).
Margolis–Nunno, H., et al., "Virus Sterilization in Platelet Concentrates with Psoralen and Ultraviolet A Light in the Presence of Quenchers," Transfusion 32:541 (1992).
Fijnheer, R., et al., "In Vitro Evaluation of Buffy–Coat–Derived Platelet Concentrates Stored in a Synthetic Medium," Vox Sang. 659:77 (1990).
Bertolini, F., et al., "Evaluation of Platelet Concentrates Prepared from Buffy Coats and Stored in a Glucose–Free Crystalloid Medium," Transfusion 29:605 (1989).
Pietersz, R. N. I., Loos, J. A. and Reesink, H. W., "Platelet Concentrates Stored in Plasma for 72 Hours at 22° C. Prepared from Buffycoats of Citrate–Phosphate–Dextrose Blood collected in a Quadruple Bag Saline–Adenine–Glucose–Mannitol System," Vox Sang. 49:81 (1985).
Bertolini, F. et al., "Platelet Quality after 15–day Storage of Platelet Concentrates Prepared from Buffy coats and Stored in a Glucose–Free Crystalloid Medium," Transfusion 32:9 (1992).
Pindur, G. et al., "Hirudin—A Potential Stabilizing Factor for Platelet Preservation in Transfusion," Haemostasis 21 (suppl 1):156 (1991).
Heaton, W. A. L., Holme, S. and Keegan, T., "Development of a Combined Storage Medium for 7–Day Storage of Platelet Concentrates and 42–Day Storage of Red Cell Concentrates," British Journal of Haematology 75:400 (1990).
Bode, A. P. and Miller, D. T., "Preservation of In Vitro Function of Platelets Stored in the Presence of Inhibitors of Platelet Activation and a Specific Inhibitor of Thrombin," J. Lab Clin Med. 111:118 (1988).
Murphy, S. et al., "Platelet Storage in Synthetic Media lacking Glucose and Bicarbonate," Transfusion 31:16 (1991).
Rock, G., et al., "Storage of Platelets in Balanced Salt Solutions: A Simple Platelet Storage Medium," Transfusion, 31:21 (1991).
Kotelba–Witkowska, B., Harmening–Pittiglio, D. M., and Schiffer, C. H., "Storage of Platelet Concentrates Using Ion Exchange Resin Charged with Dibasic Phosphate," Blood 58:537 (1981).
Murphy, S. et al., "Acetate Can Replace Bicarbonate in a Platelet storage Medium," Transfusion :351a (1991).
Murphy, S., et al., "Storage of Platelet Concentrates (PC) in Plasma and Synthetic Medium a New Polyvinyl Chloride (PVC) Container," Transfusion :404a (1991).
Rebulla, P., et al., "Platelet Concentrates Prepared from Pooled Buffy–coats and Stored in a Glucose–free Crystalloid Medium. The Milan Experience," Transfus. Sci. 11:357 (1990).
Murphy, S., et al., "Platelet Storage in a Synthetic Medium (PSM)," Transfusion 26:568 (1986).
Adams, G. A., and Rock, G., "Storage of Human Platelet Concentrates in an Artificial Medium without Dextrose," Transfusion 28:217 (1988).
Holme, S., et al., "Improved in Vivo and in Vitro Viability of Platelet Concentrates Stored for Seven Days in a Platelet Additive Solution," British Journal of Haematology 66:233 (1987).
Adams, G. A., et al., "Survival and Recovery of Human Platelets Stored for Five Days in a Non–Plasma Medium," Blood 67:672 (1986).
Holme, S., et al., "Improved Platelet in Vivo Viability Following 14 Days of Storage Using a Synthetic Medium with Inhibitors," Blood 74:42a (1989).
Grana, et al., "Use of 8–Methoxypsoralen and Ultraviolet–A Pretreated Concentrates to prevent Alloimmunization Against Class I Major Histocompatibility Antigens," Blood 77:2530 (1991).
Lin, Lily, Use of 8–MOP & Long Wavelength UV Radiation . . . Blood vol. 74 #1 Jul. 1989 pp. 517–525.
Margolis–Numno M. Photochemical Virus Sterilization . . . Thromb Haemostas 65:1162 (1991).

SYNTHETIC MEDIA COMPOSITIONS AND METHODS FOR INACTIVATING BACTERIA AND VIRUSES IN BLOOD PREPARATIONS WITH 8-METHOXYPSORALEN The present application is a continuation of U.S. application Ser. No. 07/926,477 filed Aug. 7, 1992, now abandoned, which is a continuation of U.S. application Ser. No. 07/844,790 filed Mar. 2, 1992, now U.S. Pat. No. 5,288,605.

FIELD OF THE INVENTION

The invention generally relates to the inactivation of contaminants in material intended for in vivo use, and in particular the inactivation of microorganisms in blood preparations.

BACKGROUND

Whole blood collected from volunteer donors for transfusion recipients is typically separated into its components: red blood cells, platelets, and plasma. Each of these fractions are individually stored and used to treat a multiplicity of specific conditions and disease states. For example, the red blood cell component is used to treat anemia; the concentrated platelet component is used to control bleeding; and the plasma component is used frequently as a source of Clotting Factor VIII for the treatment of hemophilia.

Ideally, all blood cell preparations should be from freshly drawn blood and then immediately transfused to the recipient. However, the logistics of operating a blood donor center preclude this possibility in the vast majority of cases. Transfusions are needed day and night and it is difficult, if not impossible, to arrange for donor recruiting at unusual hours. Consequently, modern blood donor centers must use stored blood products.

In the United States, blood storage procedures are subject to regulation by the government. The maximum storage periods for the blood components collected in these systems are specifically prescribed. For example, whole blood components collected in an "open" (i.e. non-sterile) system must, under governmental rules, be transfused within twenty-four hours and in most cases within six to eight hours. By contrast, when whole blood components are collected in a "closed" (i.e. sterile) system the red blood cells can be stored up to forty-two days (depending upon the type of anticoagulant and storage medium used) and plasma may be frozen and stored for even longer periods.

Murphy and Gardner, New Eng.J.Med. 280:1094 (1969), demonstrated that platelets stored as platelet-rich plasma (PRP) at 22° C. possessed a better in vivo half-life than those stored at 4° C. Thus, more acceptable platelet concentrates could be transfused after storage at room temperature. Until recently, the rules allowed for platelet concentrate storage at room temperature for up to seven days (depending upon the type of storage container). However, it was recognized that the incidence of bacterial growth and subsequent transfusion reactions in the recipient increased to unacceptable levels with a seven day old platelet concentrate. Platelet concentrates may now be stored for no more than five days.

Blood bags used for platelet concentrate preparation are in themselves sterile, as are the connected satellite bags. One might believe, therefore, that it is a relatively simple matter to keep the blood preparation sterile during the manipulations needed to concentrate the platelets. However, bacteria can be introduced by at least two different means. First, if the donor is experiencing a mild bacteremia, the blood will be contaminated, regardless of the collection or storage method. Adequate donor histories and physicals will decrease but not eliminate this problem. See B. J. Grossman et al., Transfusion 31:500 (1991). A second, more pervasive source of contamination is the venepuncture. Even when "sterile" methods of skin preparation are employed, it is extremely difficult to sterilize the crypts around the sweat glands and hair follicles. During venepuncture, this contaminated skin is often cut out in a small "core" by a sharp needle. This core can serve to "seed" the blood bag with bacteria that may grow and become a risk to the recipient.

Indeed, many patients requiring platelet transfusions lack host-defense mechanisms for normal clearing and destruction of bacteria because of either chemotherapy or basic hematologic disease. The growth of even seemingly innocuous organisms in stored platelets can, upon transfusion, result in recipient reaction and death. See e.g. B. A. Myhre JAMA 244:1333 (1980). J. M. Heal et al. Transfusion 27:2 (1987).

The reports assessing the extent of contamination in platelets have differed in their methods, sample size, and bacterial detection schemes. D. H. Buchholz, et al., Transfusion 13:268 (1973) reported an overall level of platelet contamination of 2.4% when a large (>1000 bags) sample was examined and extensive measures were taken for bacterial culturing. While some units were heavily contaminated after just 24 hours of storage, the incidence as a whole varied according to the age of the concentrate and increased with the widespread practice of pooling individual units; over 30% of pools were contaminated at 3 days. See also D. H. Buccholz, et al., New Eng. J. Med. 285:429 (1971). While other clinicians suggest lower numbers, recent studies indicate that septic platelet transfusions are significantly underreported. See e.g. J. F. Morrow et al. JAMA 266:555 (1991).

Pre-culturing platelets is not a solution to the bacterial contamination problem. The culture assay takes 48 hours to detect growth. Holding platelet units for an additional two days to await the results of the assay would create, ironically, a smaller margin of safety. See Table 2 in J. F. Morrow et al. JAMA 266:555 (1991). While heavily contaminated units would be detected at the outset, lightly contaminated units would be allowed to grow for two days. Older and potentially more contaminated units would end up being transfused.

Washing the blood cells (e.g. with saline) or filtering the bacteria are also not practical solutions. These techniques are time consuming and inefficient, as they can reduce the number of viable blood cells available for transfusion. Most importantly, they typically involve an "entry" into the storage system. Once an entry is made in a previously closed system, the system is considered "opened," and transfusion must occur quickly, regardless of the manner in which the blood was collected and processed in the first place.

Finally, antibiotics are not a reasonable solution. Contamination occurs from a wide spectrum of organisms. Antibiotics would be needed to cover this spectrum. Many recipients are allergic to antibiotics. In addition, there is an every increasing array of drug-resistant strains of bacteria that would not be inactivated.

In sum, there is a need for a means of inactivating bacteria from blood components prior to storage and transfusion storage in a way that lends itself to use in a closed system. This approach must be able to handle a variety of organisms without harm to the blood product or the transfusion recipient.

SUMMARY OF THE INVENTION

The present invention relates to methods for treating contaminants in material intended for in vivo use, and in particular blood and blood products for human use. In accordance with the present invention, a nucleic acid binding compound is selectively employed to treat contamination by microorganisms. In one embodiment, the present invention contemplates a method of inactivation microorganisms in blood preparations prior to long term storage and transfusion, comprising: a) providing, in any order, i) 8-methoxypsoralen; ii) means for activating 8-methoxypsoralen; iii) a blood preparation in a synthetic media; b) adding 8-methoxypsoralen to the blood preparation at a final concentration of approximately 30 ug/ml or less; and c) activating 8-methoxypsoralen, so that the nucleic acid binding compounds bind covalently to the nucleic acid of a portion of the microorganisms.

The method of the present invention is particularly useful where the microorganisms comprise single cell and multicellular organisms, such as bacteria, fungi, mycoplasma and protozoa. The present invention is employed with success with platelets.

In a preferred embodiment, the activating means comprises a photoactivation device capable of emitting a given intensity of a spectrum of electromagnetic radiation comprising wavelengths between 180 nm and 400 nm. Preferably, the intensity is less than 20 $mW/cm^2$ and the blood preparation is exposed to this intensity for less than ten minutes. In one embodiment, the blood preparation is exposed to this intensity for only approximately five minutes.

It is not intended that the present invention be limited to particular nucleic acid binding compounds. In one embodiment, the present invention contemplates photoreactive nucleic acid binding compounds selected from the group comprising furocoumarins. In a preferred embodiment, the furocoumarin is a psoralen, such as 8-methoxypsoralen.

The present invention also contemplates compositions having anti-microbial properties. In one embodiment, the composition comprises 8-methoxypsoralen at a concentration less than 30 ug/ml and material intended for human in vivo use together in a synthetic media. Preferably, the concentration is approximately 5 ug/ml.

The present invention also contemplates using nucleic acid binding compounds in combination with other reagents. In particular, the present invention contemplates adding mannitol to the synthetic media to preserve platelet function.

DESCRIPTION OF THE INVENTION

Figure 1:
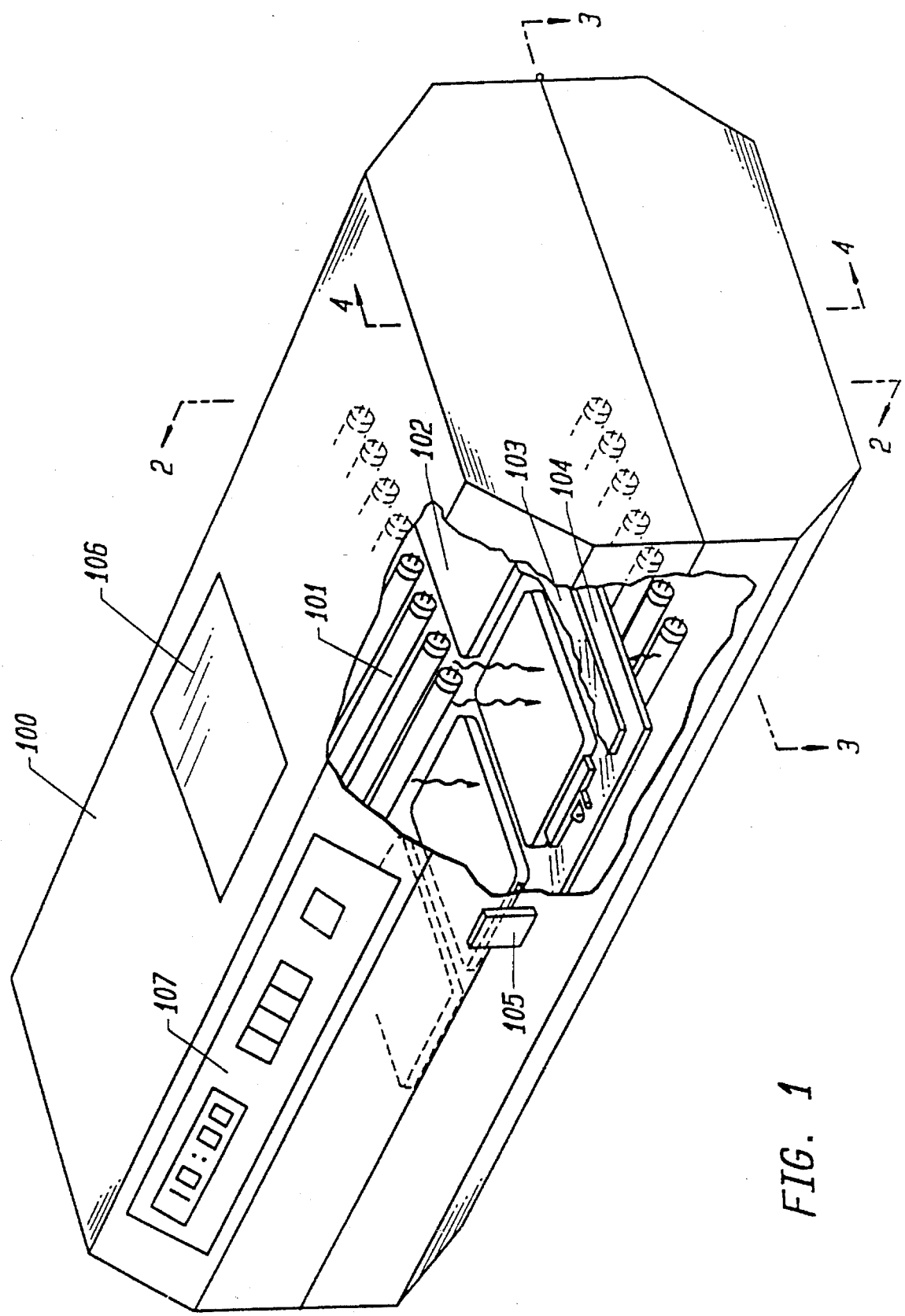
FIG. 1 is a perspective view of one embodiment of the device of the present invention.

The present invention relates to methods for treating contaminants in material intended for in vivo use, and in particular blood and blood products. In one embodiment, the method of the present invention comprises the treatment of platelet concentrates for contamination by microorganisms.

As noted previously, whole blood is collected and typically separated into red blood cells, platelets, and plasma. Each of these fractions are individually stored under specific conditions prior to in vivo use. In many cases, the extent of contamination is related to the storage time because of growth. A process that inactivated microorganisms at the time of blood collection would be expected to prevent growth during storage.

In one embodiment, the present invention contemplates inactivating blood products after separation but before storage. In this embodiment, a nucleic acid binding compound is selectively employed to treat contamination by microorganisms.

In one embodiment, the nucleic acid binding compound is selected from the group comprising furocoumarins. In a preferred embodiment, the furocoumarin is a psoralen that is activated by a photoactivation device.

Psoralens are tricyclic compounds formed by the linear fusion of a furan ring with a coumarin. Psoralens can intercalate between the base pairs of double-stranded nucleic acids, forming covalent adducts to pyrimidine bases upon absorption of longwave ultraviolet light (UVA). G. D. Cimino et al., Ann. Rev. Biochem. 54:1151 (1985). Hearst et al., Quart. Rev. Biophys. 17:1 (1984). If there is a second pyrimidine adjacent to a psoralen-pyrimidine monoadduct and on the opposite strand, absorption of a second photon can lead to formation of a diadduct which functions as an interstrand crosslink. S. T. Isaacs et al., Biochemistry 16:1058 (1977). S. T. Isaacs et al., Trends in Photobiology (Plenum) pp. 279–294 (1982). J. Tessman et al., Biochem. 24:1669 (1985). Hearst et al., U.S. Pat. Nos. 4,124,589, 4,169,204, and 4,196,281, hereby incorporated by reference.

Psoralens have been shown to inactivate viruses in some blood products. See H. J. Alter et. al., The Lancet (ii:1446) (1988). L. Linet al., Blood 74:517 (1989). G. P. Wiesehahn et al., U.S. Pat. Nos. 4,727,027 and 4,748,120, hereby incorporated by reference, describe the use of a combination of 8-methoxypsoralen (8-MOP) and irradiation. They show that 300 ug/ml of 8-MOP together with one hour or more of irradiation with ultraviolet light can effectively inactivate viruses. However, these treatment conditions cause harm to the blood product because of energy transfer. Their approach is only feasible if the damage to cells is specifically suppressed by limiting the concentration of molecular oxygen, a difficult and expensive process.

The inactivation method of the present invention provides a method of inactivating single cell and multicellular organisms, and in particular, bacteria, fungi, mycoplasma and protozoa. In contrast to previous approaches, the method of the present invention does not cause harm to the blood product. There is no significant damage to cells and, therefore, no need to limit the concentration of molecular oxygen.

The present invention contemplates using much lower concentrations of nucleic acid binding compounds than previously employed. For example, the present invention contemplates using 8-MOP at concentrations of 30 ug/ml or less. Indeed, a preferred concentration of 8-MOP for bacterial decontamination in platelet concentrates is 3 ug/ml or less, i.e. a one hundredfold lower concentration than employed by G.P. Wiesehahn et al. supra.

The present invention, furthermore, contemplates using much lower doses of irradiation than previously described. This is accomplished with lower intensity irradiation sources, with wavelength cutoff filters (see below), and/or shorter irradiation times. In a preferred embodiment, the time of irradiation is variable and controlled from 1 second to 99 minutes, in one second increments.

In one embodiment, the device of the present invention is mounted on an agitator, giving horizontal unidirectional and sinusoidal motion of variable frequency and amplitude. In another embodiment, heat from the lamps, ballasts and other sources is blocked from the bags.

While it is not intended that the present invention be limited by the theory of inactivation, the use of lower compound concentrations and irradiation doses comes from and understanding that, where the present invention is applied to the decontamination of a single cell or multicellular organism (as opposed to a virus), a lower level of nucleic acid binding will achieve inactivation. In addition, it is recognized that it is not essential that inactivation be complete. That is to say, partial inactivation will be adequate as long as the viable portion is unable, within the storage period, to grow to levels sufficient to cause disease.

To appreciate that, in any given case, an inactivation method may or may not achieve complete inactivation, it is useful to consider a specific example. A bacterial culture is said to be sterilized if an aliquot of the culture, when transferred to a fresh culture plate and permitted to grow, is undetectable after a certain time period. The time period and the growth conditions (e.g. temperature) define an "amplification factor". This amplification factor along with the limitations of the detection method (e.g. visual inspection of the culture plate for the appearance of a bacterial colony) define the sensitivity of the inactivation method. A minimal number of viable bacteria must be applied to the plate for a signal to be detectable. With the optimum detection method, this minimal number is 1 bacterial cell. With a suboptimal detection method, the minimal number of bacterial cells applied so that a signal is observed may be much greater than 1. The detection method determines a "threshold" below which the method appears to be completely effective (and above which the method is, in fact, only partially effective).

This interplay between the amplification factor of an assay and the threshold that the detection method defines, can be illustrated. For example, bacterial cells can be applied to a plate; the detection method is arbitrarily chosen to be visual inspection. Assume the growth conditions and time are such that an overall amplification of $10^4$ has occurred. The detectable signal will be proportional to the number of bacterial cells actually present after amplification. For calculation purposes, the detection threshold is taken to be $10^6$ cells; if fewer than $10^6$ cells are present after amplification, no cell colonies are visually detectable and the inactivation method will appear effective. Given the amplification factor of $10^4$ and a detection threshold of $10^6$, the sensitivity limit would be 100 bacterial cells; if less than 100 viable bacterial cells were present in the original aliquot of the bacterial culture after the sterilization method is performed, the culture would still appear to be sterilized.

Such a situation is common for bacterial growth assays. The sensitivity of the assay is such that viable bacterial cells are present but the assay is unable to detect them. This may explain, at least in part, the variability in results obtained by researchers attempted to determine the extent of bacterial contamination of blood products. See D. H. Buchholz, et al., Transfusion 13:268 (1973), wherein such variability is discussed.

It should be noted that, in many countries, contamination of blood products by cellular organisms is more pervasive and, therefore, more serious than viral contamination. For example, in South America, the most important blood-borne organism is *T. cruzi*, which is the etiologic agent of Chagas disease. Approximately 16–18 million people are infected in the Americas (including 11% of the population of Chile). It is contemplated that the decontamination method of the present invention is well-suited for inactivation of this protozoa.

The present invention contemplates devices and methods for photoactivation and specifically, for activation of photoreactive nucleic acid binding compounds. The present invention contemplates devices having an inexpensive source of electromagnetic radiation that is integrated into a unit. In general, the present invention contemplates a photoactivation device for treating photoreactive compounds, comprising: a) means for providing appropriate wavelengths of electromagnetic radiation to cause activation of at least one photoreactive compound; b) means for supporting a plurality of blood products in a fixed relationship with the radiation providing means during activation; and c) means for maintaining the temperature of the blood products within a desired temperature range during activation. The present invention also contemplates methods, comprising: a) supporting a plurality of blood product containers, containing one or more photoreactive compounds, in a fixed relationship with a fluorescent source of electromagnetic radiation; b) irradiating the plurality of blood products simultaneously with said electromagnetic radiation to cause activation of at least one photoreactive compound; and c) maintaining the temperature of the blood products within a desired temperature range during activation.

The major features of one embodiment of the device of the present invention involve: A) an inexpensive source of ultraviolet radiation in a fixed relationship with the means for supporting the sample vessels, B) rapid photoactivation, C) large sample processing, D) temperature control of the irradiated samples, and E) inherent safety.

A. Electromagnetic Radiation Source

A preferred photoactivation device of the present invention has an inexpensive source of ultraviolet radiation in a fixed relationship with the means for supporting the sample vessels. Ultraviolet radiation is a form of energy that occupies a portion of the electromagnetic radiation spectrum (the electromagnetic radiation spectrum ranges from cosmic rays to radio waves). Ultraviolet radiation can come from many natural and artificial sources. Depending on the source of ultraviolet radiation, it may be accompanied by other (non-ultraviolet) types of electromagnetic radiation (e.g. visible light).

Particular types of ultraviolet radiation are herein described in terms of wavelength. Wavelength is herein described in terms of nanometers ("nm"; $10^{-9}$ meters). For purposes herein, ultraviolet radiation extends from approximately 180 nm to 400 nm. When a radiation source, by virtue of filters or other means, does not allow radiation below a particular wavelength (e.g. 320 nm), it is said to have a low end "cutoff" at that wavelength (e.g. "a wavelength cutoff at 300 nanometers"). Similarly, when a radiation source allows only radiation below a particular wavelength (e.g. 360 nm), it is said to have a high end "cutoff" at that wavelength (e.g. "a wavelength cutoff at 360 nanometers").

For any photochemical reaction it is desired to eliminate or least minimize any deleterious side reactions. Some of these side reactions can be caused by the excitation of endogenous chromophores that may be present during the photochemical activation procedure. In a system where only nucleic acid and psoralen are present, the endogenous chromophores are the nucleic acid bases themselves. Restricting the activation process to wavelengths greater than 320 nm minimizes direct nucleic acid damage since there is very little absorption by nucleic acids above 313 nm.

In blood products, the nucleic acid is typically present together with additional biological chromophores. If the biological fluid is just protein, the 320 nm cutoff will be adequate for minimizing side reactions (aromatic amino acids do not absorb above 320 nm). If the biological fluid includes cells and/or cellular constituents, there will be many other chromophores, including hemes and flavins.

Hemes are abundant in blood products where they arise from the lysis of red cells. Flavins, like hemes, are required for metabolic respiration. Both of these endogenous chromophores will cause damage to cells if excited by photoirradiation.

Hemes have three principle absorption bands: two are in the red region of the visible spectrum; the other is centered about 400 nm. Flavins have two principle absorption peaks: one at 450 nm and the other at 370 nm.

In view of the presence of these endogenous chromophores in blood products, it is intended that the device of the present invention be designed to allow for irradiation within a small range of specific and desirable wavelengths, and thus avoid damage to cells caused by energy transfer. The preferred range of desirable wavelengths is between 320 and 350 nm.

Some selectivity can be achieved by choice of commercial irradiation sources. For example, while typical fluorescent tubes emit wavelengths ranging from 300 nm to above 400 nm (with a broad peak centered around 360 nm), BLB type fluorescent lamps are designed to remove wavelengths above 400 nm. This, however, only provides an upper end cutoff.

In a preferred embodiment, the device of the present invention comprises an additional filtering means. In one embodiment, the filtering means comprises a glass cut-off filter, such as a piece of Cobalt glass. In another embodiment, the filtering means comprises a liquid filter solution that transmit only a specific region of the electromagnetic spectrum, such as an aqueous solution of $Co(No_3)_2$. This salt solution yields a transmission window of 320–400 nm. In a preferred embodiment, the aqueous solution of $Co(No_3)_2$ is used in combination with $NiSO_4$ to remove the 365 nm component of the emission spectrum of the fluorescent or arc source employed. The Co—Ni solution preserves its initial transmission remarkably well even after tens of hours of exposure to the direct light of high energy sources.

It is not intended that the present invention be limited by the particular filter employed. Several inorganic salts and glasses satisfy the necessary requirements. For example, cupric sulfate is a most useful general filter for removing the infra-red, when only the ultraviolet is to be isolated. Its stability in intense sources is quite good. Other salts are known to one skilled in the art. Aperture or reflector lamps may also be used to achieve specific wavelengths and intensities.

When ultraviolet radiation is herein described in terms of irradiance, it is expressed in terms of intensity flux (milliwatts per square centimeter or "mW $cm^{-2}$"). "Output" is herein defined to encompass both the emission of radiation (yes or no; on or off) as well as the level of irradiance. In a preferred embodiment, intensity is monitored at 4 locations: 2 for each side of the plane of irradiation.

A preferred source of ultraviolet radiation is a fluorescent source. Fluorescence is a special case of luminescence. Luminescence involves the absorption of electromagnetic radiation by a substance and the conversion of the energy into radiation of a different wavelength. With fluorescence, the substance that is excited by the electromagnetic radiation returns to its ground state by emitting a quantum of electromagnetic radiation. While fluorescent sources have heretofore been thought to be of too low intensity to be useful for photoactivation, in one embodiment the present invention employs fluorescent sources to achieve results thus far achievable on only expensive equipment.

As used here, fixed relationship is defined as comprising a fixed distance and geometry between the sample and the light source during the sample irradiation. Distance relates to the distance between the source and the sample as it is supported. It is known that light intensity from a point source is inversely related to the square of the distance from the point source. Thus, small changes in the distance from the source can have a drastic impact on intensity. Since changes in intensity can impact photoactivation results, changes in distance are avoided in the devices of the present invention. This provides reproducibility and repeatability.

Geometry relates to the positioning of the light source. For example, it can be imagined that light sources could be placed around the sample holder in many ways (on the sides, on the bottom, in a circle, etc.). The geometry used in a preferred embodiment of the present invention allows for uniform light exposure of appropriate intensity for rapid photoactivation. The geometry of a preferred device of the present invention involves multiple sources of linear lamps as opposed to single point sources. In addition, there are several reflective surfaces and several absorptive surfaces. Because of this complicated geometry, changes in the location or number of the lamps relative to the position of the samples to be irradiated are to be avoided in that such changes will result in intensity changes.

B. Rapid Photoactivation

The light source of the preferred embodiment of the present invention allows for rapid photoactivation. The intensity characteristics of the irradiation device have been selected to be convenient with the anticipation that many sets of multiple samples may need to be processed. With this anticipation, a fifteen minute exposure time or less is a practical goal.

In designing the devices of the present invention, relative position of the elements of the preferred device have been optimized to allow for fifteen minutes of irradiation time, so that, when measured for the wavelengths between 320 and 350 nanometers, an intensity flux greater than approximately 1 mW $cm^{-2}$ is provided to the sample vessels. In a preferred embodiment, the device irradiates both sides of the bag.

C. Processing of Large Numbers of Samples

As noted, another important feature of the photoactivation devices of the present invention is that they provide for the processing of large numbers of samples. In this regard, one element of the devices of the present invention is a means for supporting a plurality of blood products, and in particular, blood bags. In the preferred embodiment of the present invention the supporting means comprises glass plates between two banks of lights with a capacity of six 50 ml bags (equivalent to Dupont Stericell bag) plus connectors and tubing, at one time. By accepting commonly used commercially available blood bags, the device of the present invention allows for convenient processing of large numbers of samples.

D. Temperature Control

As noted, one of the important features of the photoactivation devices of the present invention is temperature control. Temperature control is important because the temperature of the sample in the sample at the time of exposure to light can dramatically impact the results. For example, conditions that promote secondary structure in nucleic acids also enhance the affinity constants of many psoralen derivatives for nucleic acids. Hyde and Hearst, Biochemistry, 17, 1251 (1978). These conditions are a mix of both solvent composition and temperature. With single stranded 5S ribosomal RNA, irradiation at low temperatures enhances the covalent addition of HMT to 5S rRNA by two fold at 4° C. compared to 20° C. Thompson et al., J. Mol. Biol. 147:417 (1981). Even further temperature induced enhancements of psoralen binding have been reported with synthetic polynucleotides. Thompson et al., Biochemistry 21:1363 (1982).

With respect to bacteria, it should be noted that repair of crosslinks occurs during irradiation. However, where a lower temperature is employed during irradiation, the bacterial repair process is supressed. Thus, a 15° C. irradiation has a significant effect on the level of inactivation that is observed.

E. Inherent Safety

Ultraviolet radiation can cause severe burns. Depending on the nature of the exposure, it may also be carcinogenic. The light source of a preferred embodiment of the present invention is shielded from the user. This is in contrast to the commercial hand-held ultraviolet sources as well as the large, high intensity sources. In a preferred embodiment, the irradiation source is contained within a housing made of material that obstructs the transmission of radiant energy (i.e. an opaque housing). No irradiation is allowed to pass to the user. This allows for inherent safety for the user.

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); gm (grams); mg (milligrams); μg (micrograms); L (liters); ml (milliliters); μl (microliters); cm (centimeters); mm (millimeters); μm (micrometers); nm (nanometers); °C. (degrees Centigrade); HPLC (High Pressure Liquid Chromatography).

EXAMPLE 1

As noted above, the present invention contemplates devices and methods for the activation of photoreactive nucleic acid binding compounds. In this example, a photoactivation device is described for decontaminating blood products according to the method of the present invention. This device comprises: a) means for providing appropriate wavelengths of electromagnetic radiation to cause activation of at least one photoreactive compound; b) means for supporting a plurality of blood products in a fixed relationship with the radiation providing means during activation; and c) means for maintaining the temperature of the blood products within a desired temperature range during activation.

FIG. 1 is a perspective view of one embodiment of the device integrating the above-named features. The figure shows an opaque housing (100) with a portion of it removed, containing an array of bulbs (101) above and below a plurality of representative blood product containing means (102) placed between plate assemblies (103, 104). The plate assemblies (103, 104) are described more fully, subsequently.

The bulbs (101), which are connectable to a power source (not shown), serve as a source of electromagnetic radiation. While not limited to the particular bulb type, the embodiment is configured to accept an industry standard, dual bipin lamp.

The housing (101) can be opened via a latch (105) so that the blood product can be placed appropriately. As shown in FIG. 1, the housing (100), when closed, completely contains the irradiation from the bulbs (101). During irradiation, the user can confirm that the device is operating by looking through a safety viewport (106) which does not allow transmission of ultraviolet light to the user.

The housing (100) also serves as a mount for several electronic components on a control board (107), including, by way of example, a main power switch, a count down timer, and an hour meter. For convenience, the power switch can be wired to the count down timer which in turn is wired in parallel to an hour meter and to the source of the electromagnetic radiation. The count down timer permits a user to preset the irradiation time to a desired level of exposure. The hour meter maintains a record of the total number of radiation hours that are provided by the source of electromagnetic radiation. This feature permits the bulbs (101) to be monitored and changed before their output diminishes below a minimum level necessary for rapid photoactivation.

Figure 2:
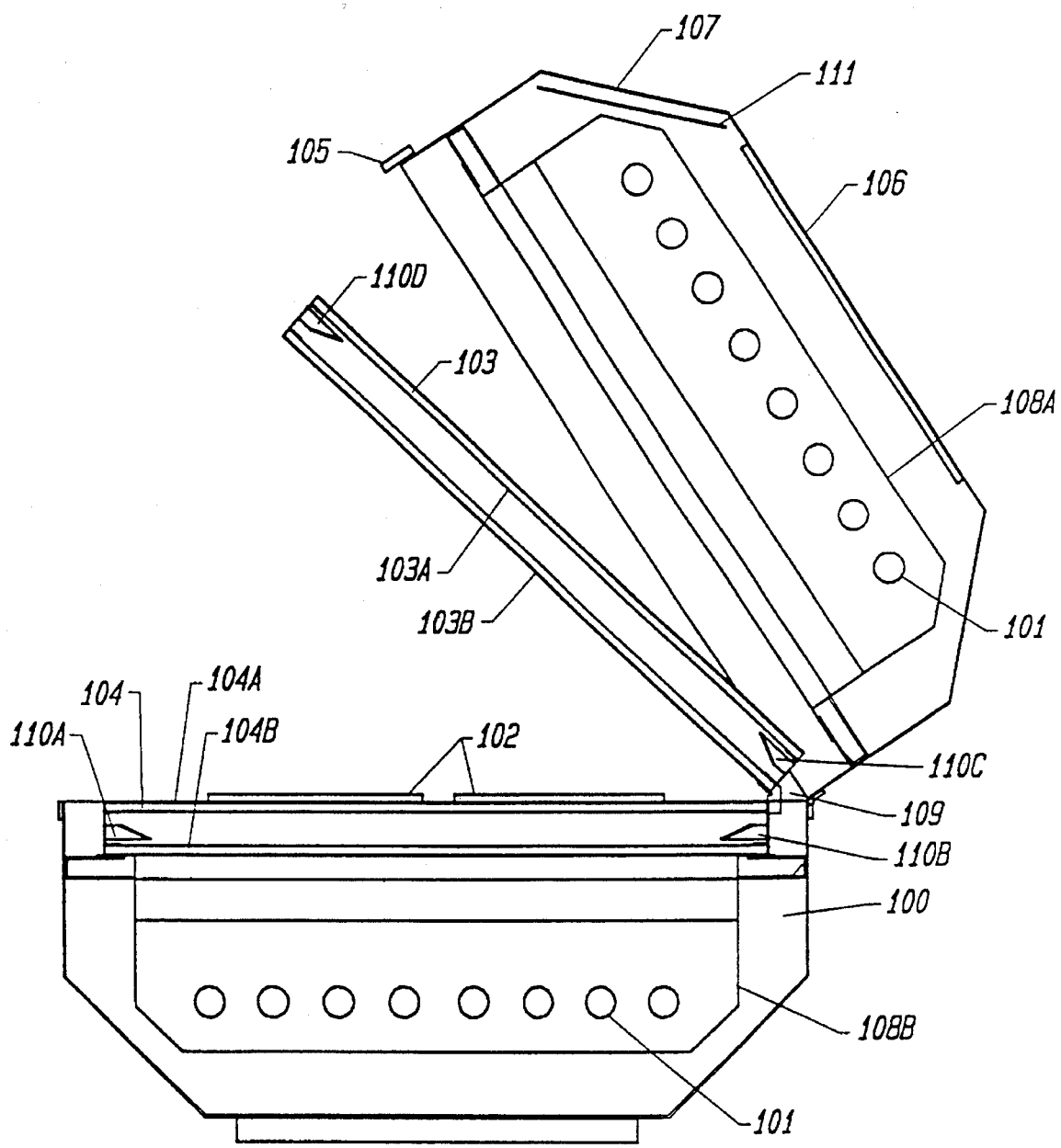
FIG. 2 is a cross-sectional view of the device shown in FIG. 1 along the lines of 2—2.

FIG. 2 is a cross-sectional view of the device shown in FIG. 1 along the lines of 2—2. FIG. 2 shows the arrangement of the bulbs (101) with the housing (100) opened. A reflector (108A, 108B) completely surrounds each array of bulbs (101). Blood product containing means (102) are placed between upper (103) and lower (104) plate assemblies. Each plate assembly is comprised of an upper (103A, 104A) and lower (103B, 104B) plates. The plate assemblies (103, 104) are connected via a hinge (109) which is designed to accommodate the space created by the blood product containing means (102). The upper plate assembly (103) is brought to rest gently on top of the blood product containing means (102) supported by the lower plate (104B) of the lower plate assembly (104).

Detectors (110A, 110B, 110C, 110D) may be conveniently placed between the plates (103A, 103B, 104A, 104B) of the plate assemblies (103, 104). They can be wired to a printed circuit board (111) which in turn is wired to the control board (107).

Figure 3:
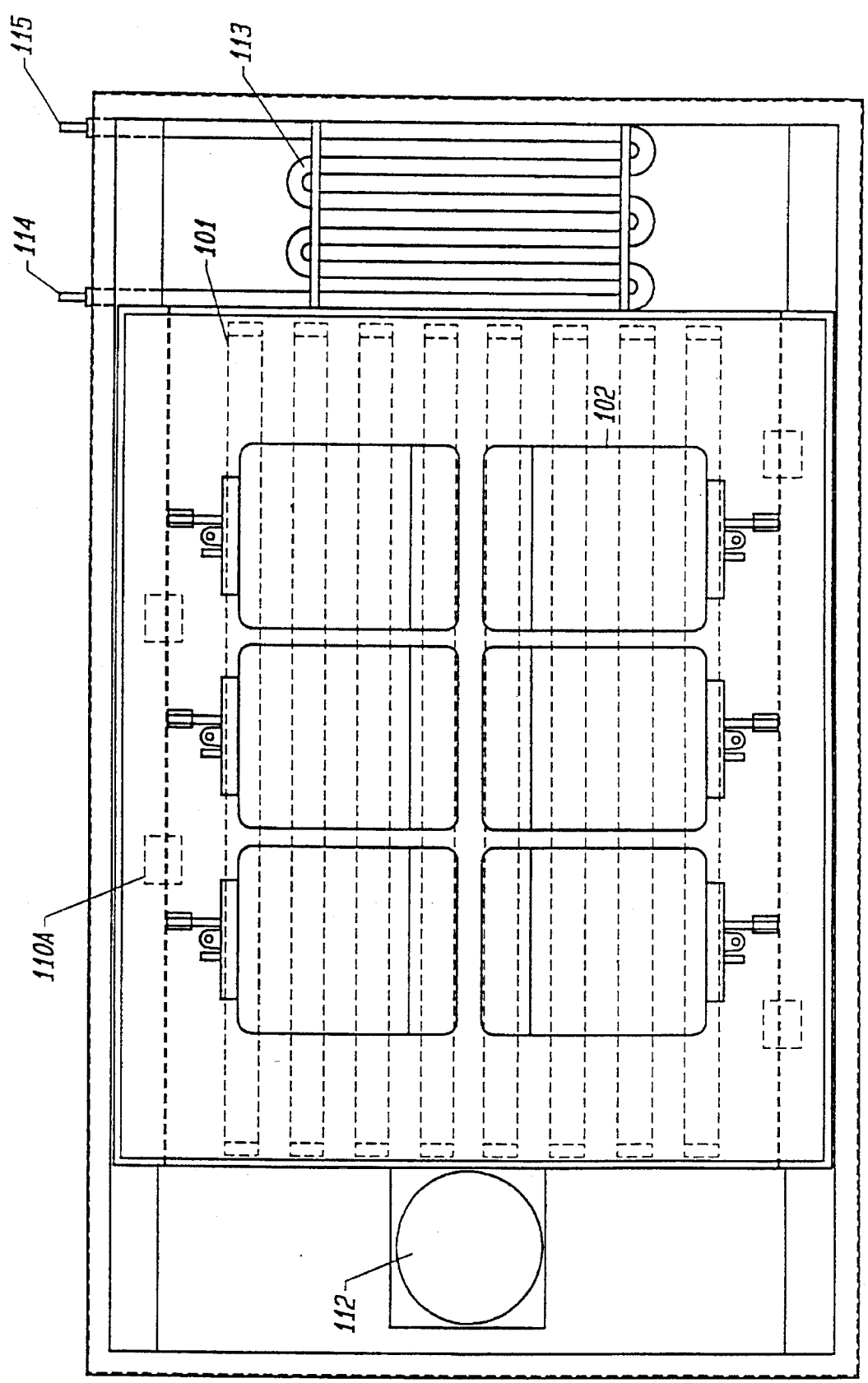
FIG. 3 is a cross-sectional view of the device shown in FIG. 1 along the lines of 3—3.

FIG. 3 is a cross-sectional view of the device shown in FIG. 1 along the lines of 3—3. Six blood product containing means (102) (e.g. teflon platelet unit bags) are placed in a fix relationship above an array of bulbs (101). The temperature of the blood product can be controlled via a fan (112) alone or, more preferably, by employing a heat exchanger (113) having cooling inlet (114) and outlet (115) ports connected to a cooling source (not shown).

Figure 4:
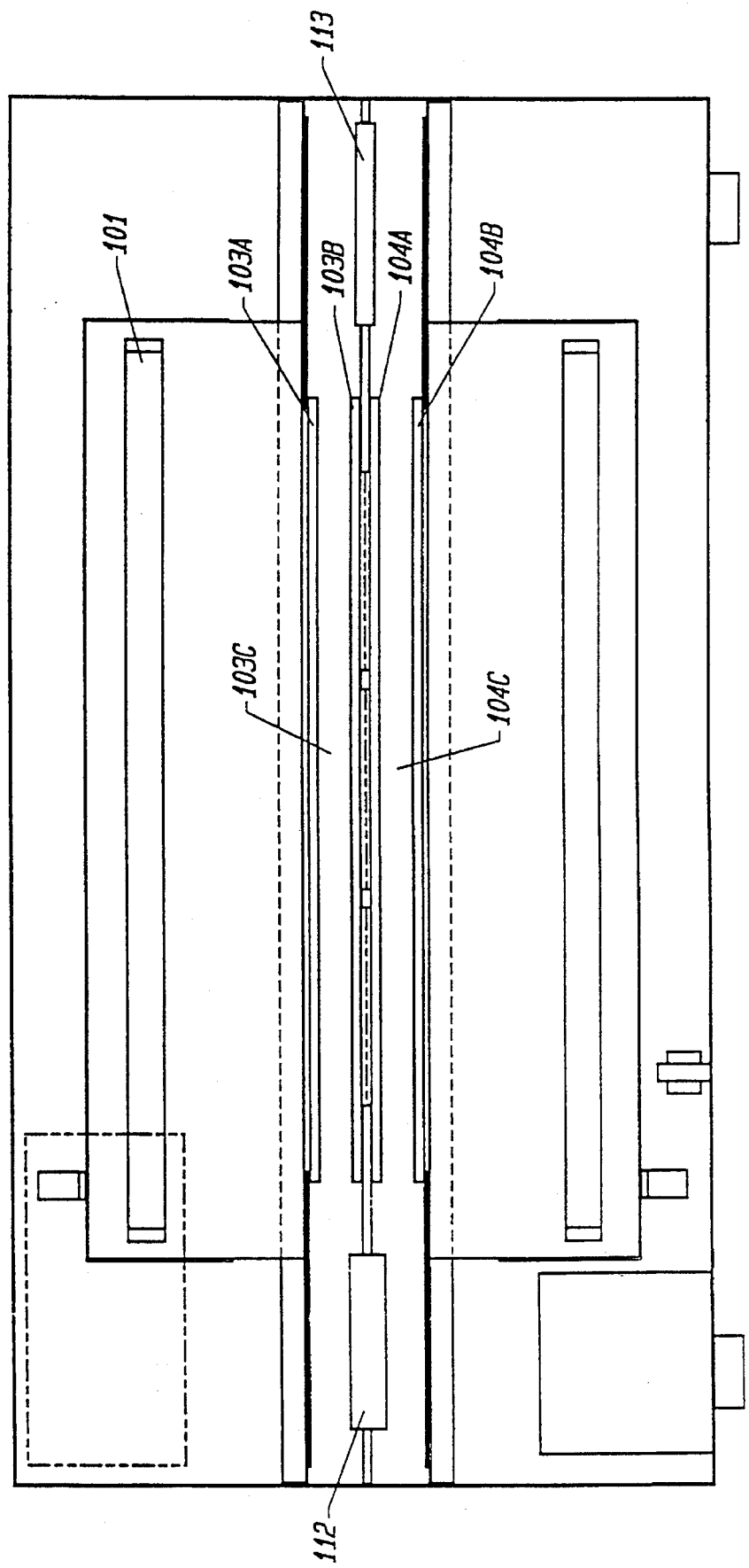
FIG. 4 is a cross-sectional view of the device shown in FIG. 1 along the lines of 4—4.

FIG. 4 is a cross-sectional view of the device shown in FIG. 1 along the lines of 4—4. FIG. 4 more clearly shows the temperature control approach of a preferred embodiment of the device. Upper plate assembly plates (103A, 103B) and lower plate assembly plates (104A, 104B) each create a temperature control chamber (103C, 104C), respectively. The fan (112) can circulate air within and between the chambers (103C, 104C). When the heat exchanger (113) is employed, the circulating air is cooled and passed between the plates (103A, 103B, 104A, 104B).

EXAMPLE 2

Figure 5:
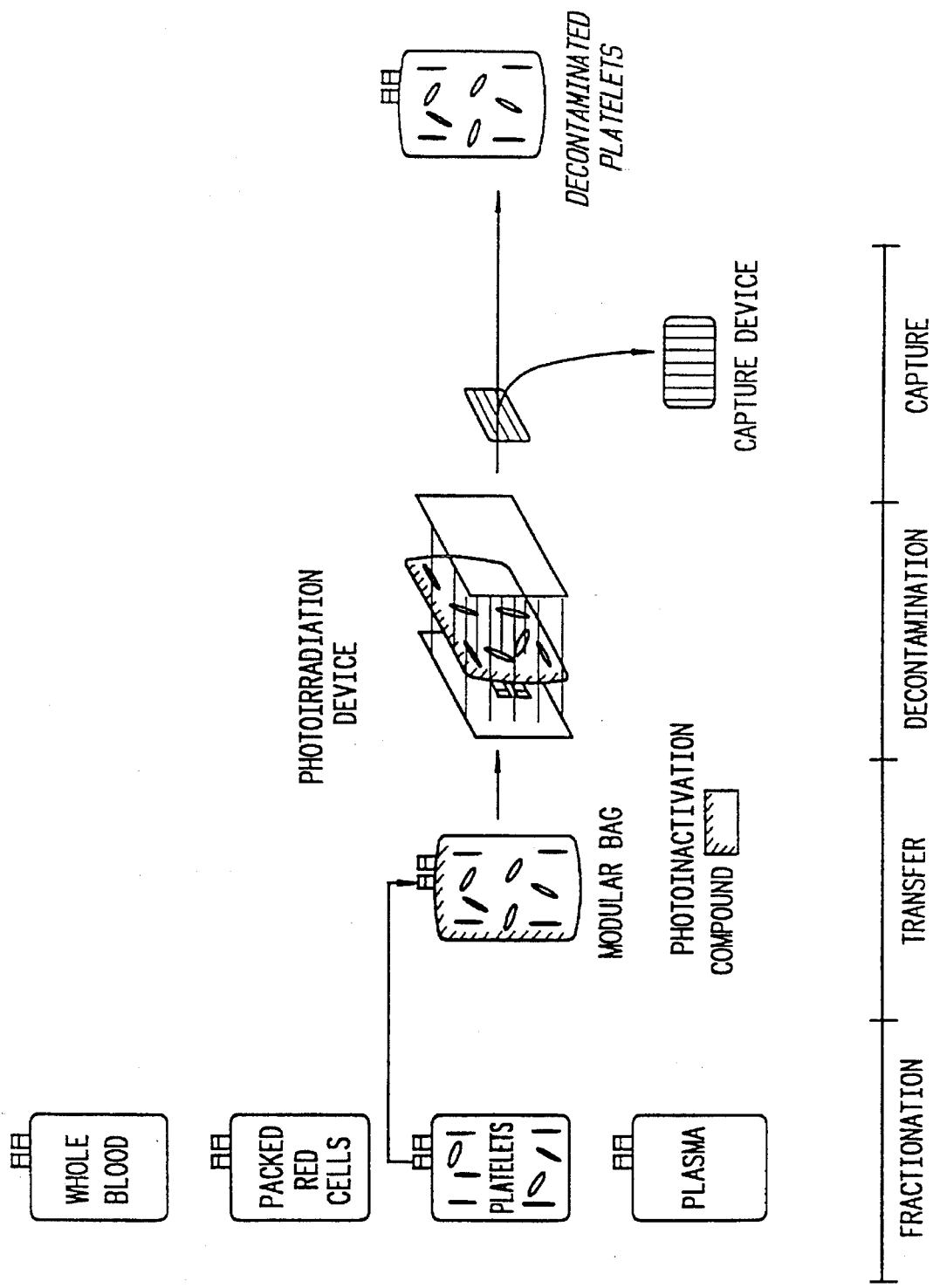
FIG. 5 schematically shows the decontamination approach of the present invention applied specifically to blood products.

FIG. 5 shows an embodiment wherein platelets are treated by the method of the present invention. Following fractionation, platelets are transferred to a bag containing a nucleic acid binding compound (shown in FIG. 1 as a shaded bag). This bag, which has transmission properties and other characteristics suited for the present invention, is then placed in an irradiation device (such as that described in Example 1, above) and is irradiated. The free compound may be collected or "captured" as desired by a capture device. In such a case, the bag would contain only compound that is contained in cells; the bag would have no free compound (this bag is indicated in FIG. 1 as unshaded).

EXAMPLE 3

In this example, the decontamination methods of the present invention are applied to inactivate *Klebsiella pneumoniae*, which is known to be among the organisms associated with bacteremia. See generally, Infect. Control 5:343 (1984). The particular isolate in this case was obtained following a platelet transfusion where the recipient immediately went into shock and later died. The platelet bag was obtained and cultured, and the organism was identified and serotyped.

For the experiment, the strain was kept at ambient temperature and inoculated onto either heart infusion agar (HIA) or heart infusion agar containing 5% (v/v) sheep blood (BAP) by swabbing each plate for confluency via a sterile applicator swab. Cultures were then incubated under static conditions for 16–18 h at 35° C. At the end of the incubation period, cultures were removed and suspended in phosphate buffered saline (PBS;pH 7.2–7.4) and spectrophotometrically standardized to 1.0 at an $OD_{610}$ using a Spectronic 501 or 601 spectrophotometer (Bausch and Lomb). After standardization, suspensions were diluted 1:10 in PBS to achieve an ca. $10^8$ CFU/ml concentration. This standardized suspension is then split to use an aliquot for the inactivation study, while another portion was plated in duplicate 10-fold serial dilutions onto HIA (or BAP) to ensure appropriate concentrations of the organism.

To assess inactivation of the organism, two ABO compatible freshly outdated human platelet concentrate units were obtained from the Blood Bank of Alameda Contra Costa Medical Association. They were pooled and redivided into two bags. One bag was infused with the bacteria preparation. The platelets in the second unit were pelleted at 1000 g for 10 minutes and then resuspended in a medium containing 85% saline and 15% plasma. Bacteria was added after platelets were well resuspended.

3 ml aliquots of bacteria containing platelet concentrate were transferred to a Teflon minibag (American Fluoroseal Corporation, Silver Spring, Maryland) and received specified amounts of 8-MOP and UVA irradiation, except for the controls, which were irradiated without psoralen, or received no treatment. Temperature was maintained at 25° C. during irradiation in the irradiation device described above which is equipped with an air cooling mechanism. BLB type bulbs were used. These are "black light" tubes (engineered to emit specific wavelengths by means of an internal phosphor coating) 24 inches in length. Total intensity is less than 15 $mW/cm^2$.

Figure 8:
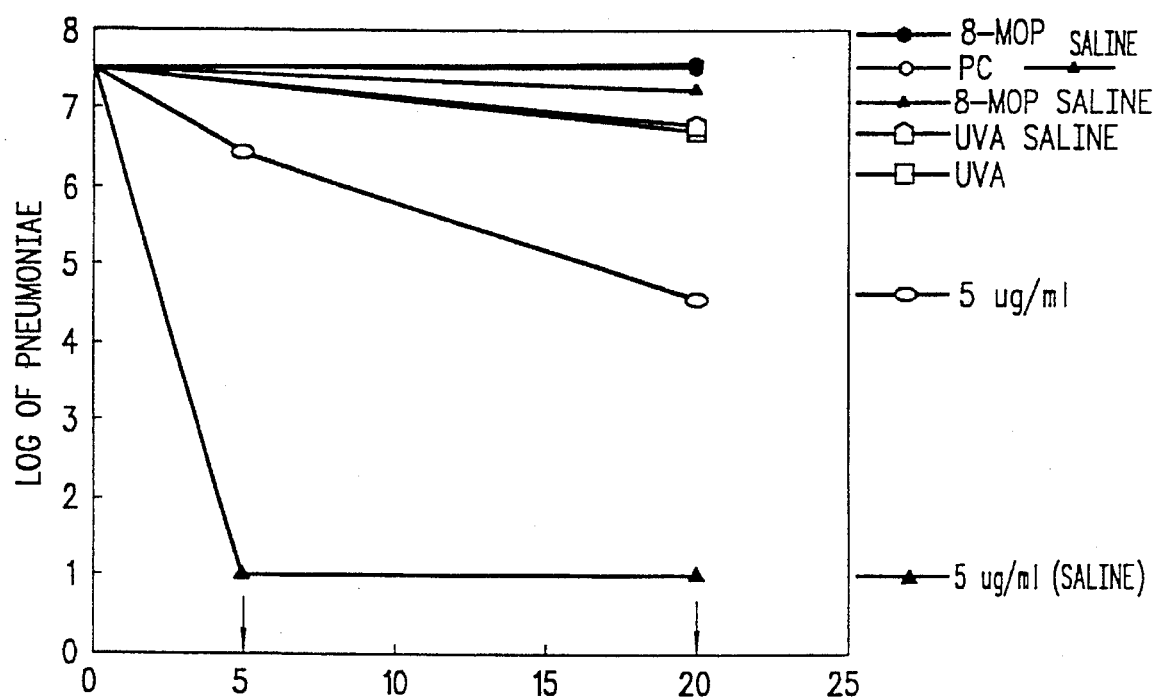
FIG. 8 is a graph showing the inactivation of gram negative bacteria.

Following irradiation, bacteria were quantified by plating 0.1 ml of serial 10-fold dilutions in broth onto 100 mm petri dishes containing BHI agar. After 24 hr incubation at 35° C., colonies were counted and bacterial concentration was calculated on a per ml basis. The results (FIG. 8) show that while only 1.2 logs of Klebsiella were killed by 5 mg/ml 8-MOP in five minutes of UVA irradiation in 100% plasma, more than 6.5 logs were killed under the same conditions in 15% plasma and 85% saline.

While not limited to any theory as to the mechanism by which this improvement in decontamination efficiency was achieved, it would appear that these results indicate that either that the optical properties of the synthetic medium are better, or the lower protein concentration allows for a higher concentration of free 8-MOP. In the latter situation, the 8-MOP would be more available for decontamination.

EXAMPLE 4

Artuc and co-workers examined the solubility of 8-0MOP in human and bovine serum proteins, and showed that at 8-MOP concentrations ranging form 100 to 1000 ng/ml. concentrations similar to those observed in patients undergoing psoralen ultraviolet A (PUVA) therapy for psoriasis, 75% to 80% of the 8-MOP was bound to albumin. M. Artuc et al., Brit. J. Derm. 101:669 (1979).

In this example, the binding of 8-MOP to Calf Thymus DNA is compared using plasma and a protein free media in order to validate the efficiency of psoralen-nucleic interactions under the decontamination methods of the present invention. Although this measurement used eukaryotic nucleic acid rather than bacterial nucleic acid, it is a useful indicator of the degree of adduct formation for bacteria.

$^3$H-8-MOP was prepared to a concentration of 115 ug/ml in ethanol at a specific activity of $4.7 \times 10^6$ CPM/microgram (hereinafter "8-MOP stock"). Thereafter 130.5 or 22 ul of 8-MOP stock (2 each) for samples containing DNA ("+DNA") and 52.2 or 8.7 ul for samples not containing DNA ("–DNA") were dried down. To +DNA samples, 40 ul of DNA stock (7.7 mg/ml) was added as well as either 460 ul plasma (day old frozen) or 450 ul Tris-EDTA ("TE") buffer. To the latter was also added 10 ul 5M NaCl. For –DNA samples (i.e. the controls), 184 ul plasma and 16 ul water was added.

The samples were mildly vortexed for approximately one hour and the counts were checked to confirm that the 8-MOP dissolved.

Each sample (100 ul) was irradiated on an HRI-100 (HRI Research Inc., Concord, Calif.) at 25° C. for 0, 2, 4, 8, and 16 minutes. Samples were kept at 4° C. overnight after irradiation. Thereafter, the samples were extracted. First, a phenol solution was prepared at pH 8 by equilibrating with 0.1 M Tris pH 8. Each sample was then extracted with 100 ul phenol. Each sample was centrifuged for 5 minutes to remove the aqueous phase to a new tube. A second extraction was performed with 100 ul 1:1 phenol:chloroform. A final extraction was performed with 100 ul chloroform.

The final aqueous phase was precipitated by adding 50 ul NaCl adjusted to give a final concentration of NaCl of 0.2 M and then adding 250 ul ethanol. The samples were again centrifuged (10 minutes). The supernatant was removed and the pellets were dried. The pellets were resuspended in 100 ul TE and reprecipitated. This was repeated for a total of 3 precipitations. The final pellets were brought up in 600 ul water and 100 ul was counted. Each sample was assayed for DNA by measuring absorbance (260 nm). 8-MOP levels were plotted as adducts per 1000 base pairs ("8-MOP-:kBP").

Figure 6:
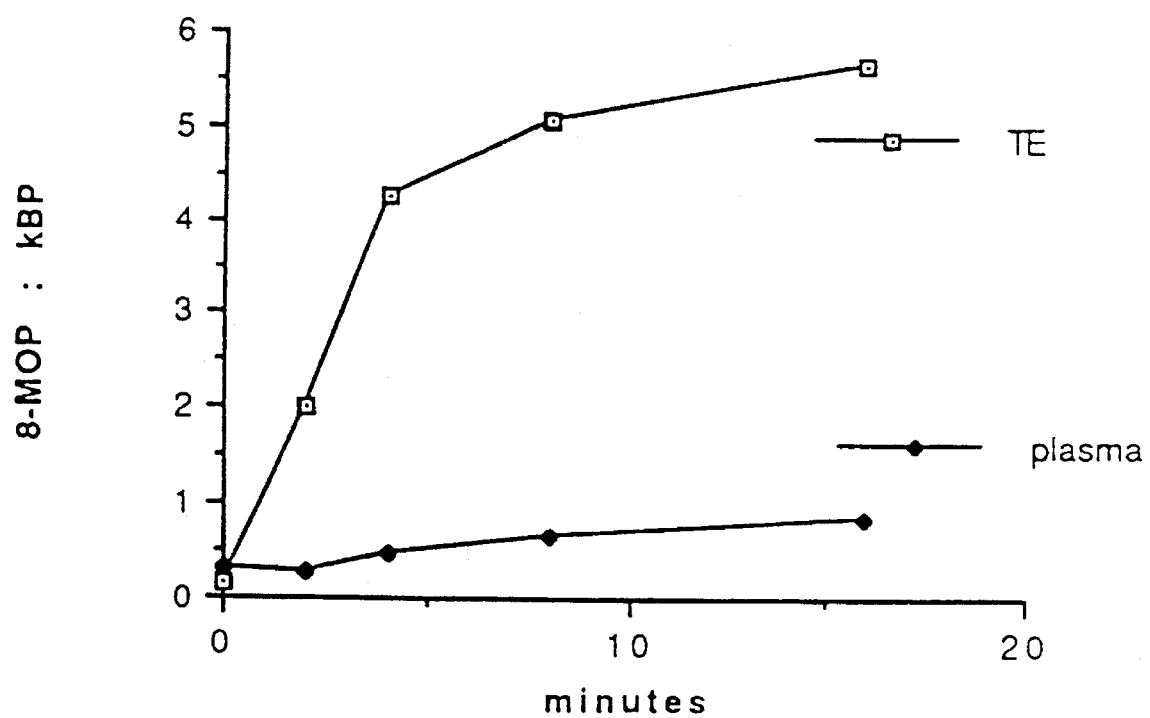
FIG. 6 is a graph showing the photoaddition of 8-methoxypsoralen to nucleic acid.

The results (FIG. 6) show that plasma does significantly change the addition kinetics of 8-MOP to DNA. Addition to nucleic acid is much better in the protein free media.

The frequency of 8-MOP-DNA adduct formation in protein free media predicts a high multiplicity of modification of the bacterial genome. Furthermore, this type of biochemical measurement has the potential to provide a means to monitor the efficiency of the photochemical inactivation method.

EXAMPLE 5

Photoactivation of psoralens and isopsoralens may result in a variety of photoproducts. "Photoproduct" is best understood by considering the possible reactions of photoreactive compound when exposed to activating wavelengths of electromagnetic radiation. While not limited to any precise mechanism, it is believed that the reaction of photoreactive compound in its ground state ("C") with activating wavelengths of electromagnetic radiation creates a short-lived excited species ("C*"):

C→C*

What happens next is largely a function of what potential reactants are available to the excited species. Since it is short-lived, a reaction of this species with nucleic acid ("NA") is believed to only be possible if nucleic acid is present at the time the excited species is generated. Thus, the reaction must, in operational terms, be in the presence of activating wavelengths of electromagnetic radiation, i.e. it is "photobinding"; it is not dark binding. The reaction can be depicted as follows:

C*+NA→NA:C

The product of this reaction is hereinafter referred to as "Photoaddition Product" and is to be distinguished from "Photoproduct."

With this reaction described, one can now consider the situation where nucleic acid is not available for binding at the time the compound is exposed to activating wavelengths of electromagnetic radiation. Since the excited species is short-lived and has no nucleic acid to react with, the excited species may simply return to its ground state:

C*→C

On the other hand, the excited species may react with itself (i.e. a ground state or excited species) to create a ground state complex ("C:C"). The product of these self-reactions where two compounds react is referred to as "photodimer" or simply "dimer." The self-reactions, however, are not limited to two compounds; a variety of multimers may be formed (trimers, etc.).

The excited species is not limited to reacting with itself. It may react with its environment, such as elements of the solvent ("E") (e.g. ions, gases, etc.) to produce other products:

C*+E→E:C

It is this type of reaction that is believed to cause cellular damage (e.g., reaction with oxygen to create singlet oxygen species). Furthermore, it may simply internally rearrange ("isomerize") to a ground state derivative ("["):

C*→[

Finally, the excited species may undergo other reactions than described here.

The present invention and the understanding of "photoproduct" does not depend on which one (if any) of these reactions actually occurs. "Photoproduct"—whatever its nature—is deemed to exist if, following the reaction of a compound and activating wavelengths of electromagnetic radiation, there is a resultant product formed that can interact with other components of the reaction environment.

With psoralens such as 4'-hydroxymethyl-4,5',8-trimethylpsoralen (HMT), there are a number of resultant products produced when the HMT is exposed to activating wavelengths of electromagnetic radiation. The major resultant products of HMT are two cyclobutyl photodimers. In one of the dimers, the two pyrone rings are linked in a cis-syn configuration, while in the other dimer, the linkage occurs between the furan end of one molecule and the pyrone end of the other, again with cis-syn configuration. A third resultant product of HMT is a monomeric HMT photoisomer. In this isomer, the central ring oxygens assume a 1, 4 instead of the normal 1, 3 orientation. While the two photodimers would not be expected to have an intercalating activity due to geometrical considerations, the photoisomer remains planer, and accordingly, it is contemplated that it has a positive intercalative association with double stranded nucleic acid and, thus, could be a mutagen.

In this example, the photochemical breakdown of 8-MOP is compared with AMT. The samples were analyzed by reverse phase HPLC using a Rainen Dynamax 300A column. Gradient elution was performed with 0.1 M ammonium acetate/acetonitrile (0–70% acetonitrile over 42 minutes). AMT elutes as a single peak at approximately 24 minutes under these conditions. Detection was by absorption at either 260 or 330 nm. The latter wavelength was used for the plasma containing samples.

Standard solutions of each compound were prepared at various concentrations. These solutions were then diluted 1:10 into water, then 300 ul injected for analysis. All samples were monitored at 300 nm. Peaks were analyzed by measuring either peak height or peak area, then converted to a gh/ml value using the standard plot. Peak area was determining by photocopying the trace, cutting out the copy of the peak, then weighing the resultant trace. The two methods gave essentially the same result.

Figure 7:
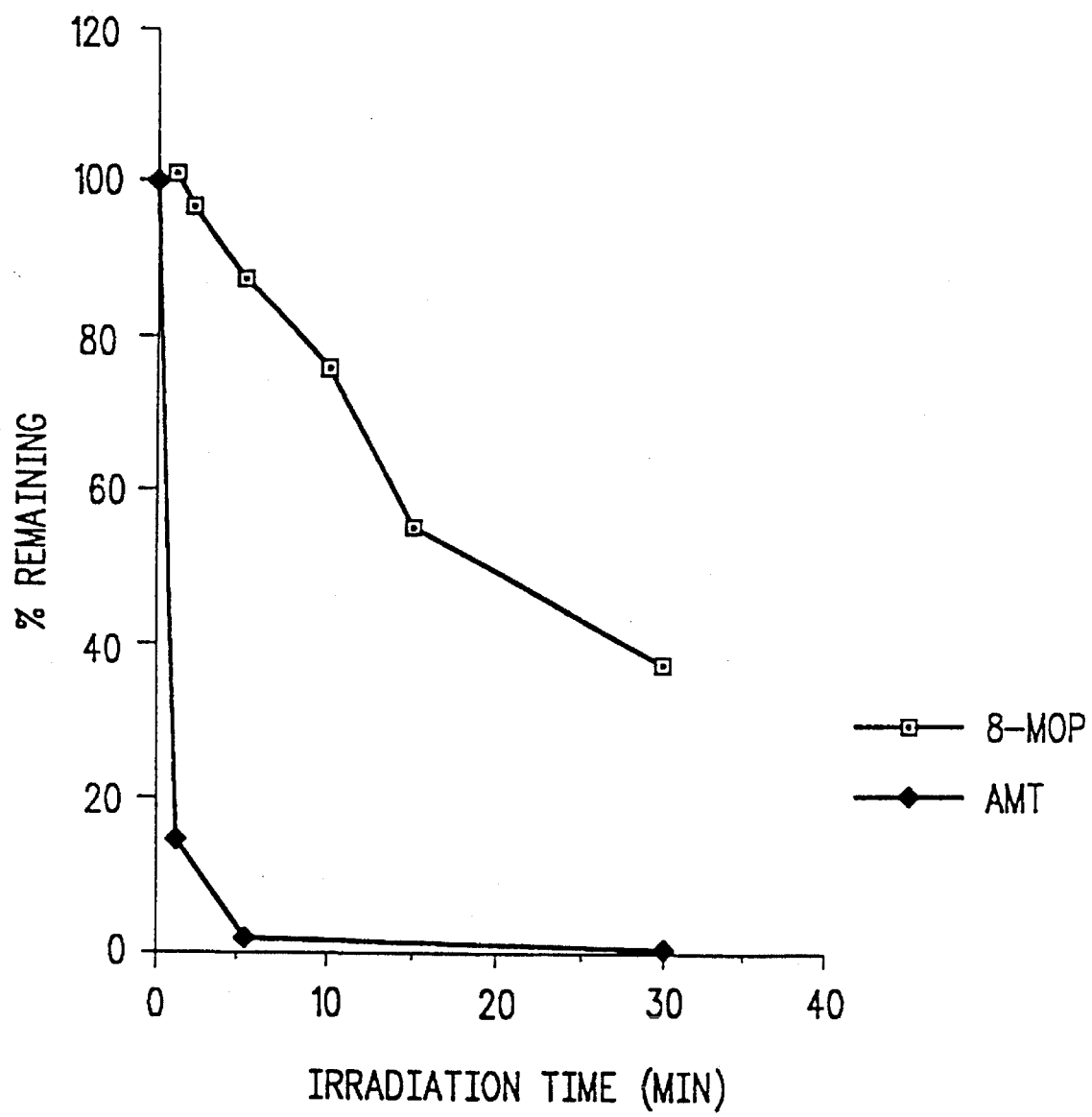
FIG. 7 is a graph showing the degradation of 8-methoxypsoralen (8-MOP) compared to that of 4'-aminomethyl-4,5', 8-trimethylpsoralen (AMT), as measured by HPLC.

The results are shown in FIG. 7. Clearly, AMT degrades more quickly than 8-MOP. It would, therefore, be expected to generate more photoproducts - which eventually would end up in the transfusion recipient. By contrast, it is not expected that 8-MOP generates a significant amount of photoproducts. This is important when one considers that the weight of authority has concluded that unactivated 8-MOP is nonmutagenic.

EXAMPLE 6

When platelets become activated, an alpha granule membrane glycoprotein called GMP140 becomes exposed on the platelet surface. Less than (5%) of fresh, normal unstimulated platelets express detectable GMP 140 levels by flow cytometry. See generally M. J. Metzelaar, *Studies on the Expression of Activation-Markers on Human Platelets* (Thesis 1991).

To measure GMP140, a small aliquot of platelet rich plasma is placed in HEPES buffer containing a GMP140-binding antibody or control mouse IgG. CD62 is a commercially available monoclonal antibody which binds to GMP 140 (available from Sanbio, Uden, the Netherlands; Caltag Labs, So. San Francisco, Calif., and Becton Dickinson, Mountain View, Calif.). After a fifteen minute incubation, Goat Anti-Mouse IgG conjugated to FITC is added to the tube in saturating amounts. Finally, the cells are diluted in isotonic saline, fixed with paraformaldehyde and analyzed on a FACSCAN (Becton Dickinson, Mountain View, Calif.). The positive control is made by adding Phorbol Myristate Acetate (PMA) to the test system at a final concentration of $10^{-7}$ M.

In this example, CD62 was employed to measure the impact, if any, of irradiation alone on platelet activation. The antibody was stored in small aliquots (0.01 mg/ml) at $-40°$ C. prior to use. A mouse IgG control (0.05 mg/ml) (Becton Dickinson, Mountain View, Calif. #9040) 5× concentrated was employed. At time of use, this was diluted 1:5 in HEPES buffer. The secondary antibody was goat Anti-Mouse IgG conjugated to FITC (TAGO, Burlingame, Calif. #3506). This was stored in small aliquots at $-20°$ C. Phorbol Myristate Acetate (PMA) (Sigma, St. Louis, Mo.) was stored at $-40°$ C. At time of use, this was dissolved in DMSO (working concentration was $1.62 \times 10^{-5}$ M).

16% Paraformaldehyde (PFA) (Sigma, St. Louis, Mo.) was prepared by adding 16 grams paraformaldehyde to 100 ml deionized water. This was heated to 70° C., whereupon 3 M NaOH was added dropwise until the solution was clear. The solution was cooled and the pH was adjusted to 7.4 with 1 N HCl. This was filtered and stored. A commercially available isotonic buffer was used: Hematall Isotonic Diluent (Fisher #CS 606-20).

For measuring platelet activation of platelet concentrates, a unit of human platelets was obtained from the Blood Bank of Alameda-Contra Costa Medical Association. 5 ml aliquots were drawn from the bag and received specified amounts of UVA irradiation, except for the control, which received no treatment other than being placed in a chamber for irradiation. Temperature was maintained at 25° C. during irradiation by placing platelet concentrate in stoppered glass water-jacketed chambers attached to a circulating water bath. The irradiation device (Derma Control, Dolton, Ill.; Model No. 1224-Special) was as described in Example 3, above. Following irradiation, the platelets were stored for 5 days. At specific time points, aliquots were taken and processed.

Processing involved adding an aliquot (e.g. 5 microliters) of platelet concentrate to each microcentrifuge tube containing the antibody and appropriate reagents and this was mixed very gently by vortex. The samples were incubated for 15 minutes at room temperature.

The Goat anti-Mouse IgG-FITC (diluted 1:10 in HEPES buffer) was added (5 microliters) to each tube and the solution was mixed by gentle vortex. The samples were incubated for an additional 15 minutes at room temperature. Isoton II was added (1 ml) to each tube and mixed gently with a polypropylene disposable pipet. 8% PFA in HEPES (150 microliters) was added to each diluted sample to final 1%. The platelets were analyzed on the FACSCAN. The results are shown in Table 1.

TABLE 1

| | Day 3 | | Day 5 | |
|---|---|---|---|---|
| Conditions | UNAC-TIVATED | PMA AC-TIVATED | UNAC-TIVATED | PMA AC-TIVATED |
| Control | 17 | 85 | 25 | 89 |
| UV 5' | 17 | 87 | 24 | 86 |
| UV 10' | 51 | 84 | 77 | 79 |

Activation is expressed as a percent. Clearly, irradiation for ten minutes (UV 10') resulted in a significant negative impact on stored platelets; the platelets were highly activated. By contrast, irradiation for five minutes (UV 5') resulted in no significant activation above the control which received no irradiation.

EXAMPLE 7

Given the results of Example 6, it is clear that either a shorter irradiation time or the use of filters is needed to avoid damage to cells by UV irradiation. In this example, CD62 is employed to measure the impact of irradiation in the presence of psoralen on platelet activation. Shorter irradiation times and wavelength filters are separately employed. Shorter Irradiation Times. A unit of human platelets is again obtained from the Blood Bank of Alameda-Contra Costa Medical Association. 5 ml aliquots are drawn from the bag to receive five minutes (5') of UVA irradiation in the presence of 10 ug/ml 8-MOP, except for the control, which receives no treatment other than being placed in a chamber for irradiation. Temperature is maintained at 25° C. during irradiation by placing platelet concentrate in stoppered glass water-jacketed chambers attached to a circulating water bath. The irradiation device (Derma Control, Dolton, Ill.; Model No. 1224-Special) is as described in Example 3, above.

Following irradiation, the platelets are again stored for 5 days as in Example 6. At specific time points, aliquots are taken and assayed with the CD62 antibody and analyzed on the FACSCAN to show that, under these conditions, platelets can be inactivated without damage to the cells and stored for five days prior to transfusion. Wavelength Filters. An aqueous solution of $Co(No_3)_2$ is used in combination with $NiSO_4$ to substantially remove the 365 nm component of the emision spectrum of the light source employed. The Co-Ni solution can be conveniently used in place of water as a coolant during the irradiation.

Following a ten minute irradiation with the filter, the platelets are stored an assayed with the CD62 antibody on the FACSCAN to show that, under these conditions, platelets can be inactivated without damage to the cells and stored for five days prior to transfusion.

EXAMPLE 8

This example involves an assessment of the impact of mannitol on platelet function in synthetic media following irradiation. Three indicators of platelet viability and function were employed: 1) maintenance of pH; 2) platelet aggregation; and 3) ATP release.

To measure pH, a commercial device was used. A small amount of platelet concentrate was introduced into a CIBA-CORNING 238 pH/Blood Gas analyzer. Platelet aggregation and ATP release were measured with a CHRONOLOG Platelet Aggregometer with a Luminescence channel. The number of platelets in samples was controlled to be constant for every measurement. A Sysmex cell counter was used to measure platelet count in the platelet samples and AB plasma was used to adjust platelet counts to 300,000 per microliter of platelet concentrate.

For the procedure, all the samples were incubated in a cap plastic tube for 30 minutes at 37° C. for activation. The optical channel is used for platelet aggregation measurement. A proportional amount of platelet concentrate and AB plasma were centrifuged at high speed (14,000 g) with a microfuge for 5 minutes in order to obtain platelet poor plasma. The aggregometer was warmed up to 37° C. The magnetic speed of the aggregometer was set at 600/min and the Gain setting was set for the luminescence channel at 0.02.

To begin, 0.45 ml of platelet poor plasma was added along with 0.5 ml of saline into a glass cuvette and placed in the PPP channel. Then 0.45 ml of platelet concentrate and 0.50 ml of saline were added to a second glass cuvette (containing a small magnet) into the sample channel. After one minute, 30 ul of Lume enzyme (Chrono-log Corp., Hayertown, Pa.) was added into the sample cuvette. After one minute, ADP and collagen reagents (10 ul) each were added to the sample cuvette. The final concentration of ADP was 10 ul and the final concentration of collagen was 5 mg/ml. Platelet aggregation and ATP release were recorded for about 8–10 minutes or until the maximum reading was reached.

An ATP standard was prepared in saline in four 10 ul aliquots (0.5, 1.0. 1.5 and 2.0 nmoles of ATP). For the ATP standard measurement, 0.45 ml of platelet concentrate and 0.5 ml of saline were added to a cuvette (containing a small magnet) into the sample channel. After one minute, 30 ul of Lume enzyme was added. After one minute, 10 ul of ATP standard was added. With the standard curve, the amount of ATP released from each sample was then determined.

For measuring platelet pH, aggregation and ATP release in this experiment, a fresh unit of human platelet concentrate was obtained from Alameda-Contra Costa Blood Bank. As a control, 3 ml was removed and transferred to a Teflon minibag. The unit was then centrifuged at room temperature for 6 minutes at 4000 rpm and then transfered to a unit press. Using an attached transfer line, 30 ml of plasma was expressed from the unit into a sterile 50 ml centrifuge tube. The expressed plasma was then replaced with 30 ml of a commercially available synthetic media, plasmalyte-A (Baxter, Ill.).

The units were allowed to rest for one hour without shaking or mixing. Following a gentle kneading of the platelet pellet to resuspend the platelets, the bag was placed back on the rotator. The volume of platelet concentrate in the plasmalyte was measured to equal 42 ml (30 ml plasmalyte and 12 ml of plasma). 38 ml plasmalyte was added to the platelet suspension to give a 15% final plasma solution.

Fifty (50) ml of the 15% plasma solution was removed. To measure platelet function after irradiation, 125 ul of a 2 mg/ml 8-MOP solution in ethanol was added to the 50 ml aliquot. After mixing, a first 16 ml aliquot was removed from the 50 ml mixture and transferred to a sterile centrifuge tube. To this tube was added 64 ul of a 0.5M mannitol solution in plasmalyte to get a final concentration of 2 mM. This platelet solution was transferred in 2.5 ml aliquots to each of 6 FL03 minibags.

A second 16 ml aliquot from the 50 ml mixture was transferred to a sterile centrifuge tube. In this case, 320 ul of a 0.5M mannitol solution was added to get a final mannitol concentration of 10 mM. This platelet solution was transferred in 2.5 ml aliquots of this platelet concentrate to each of six (6) Teflon minibags.

Figure 9:
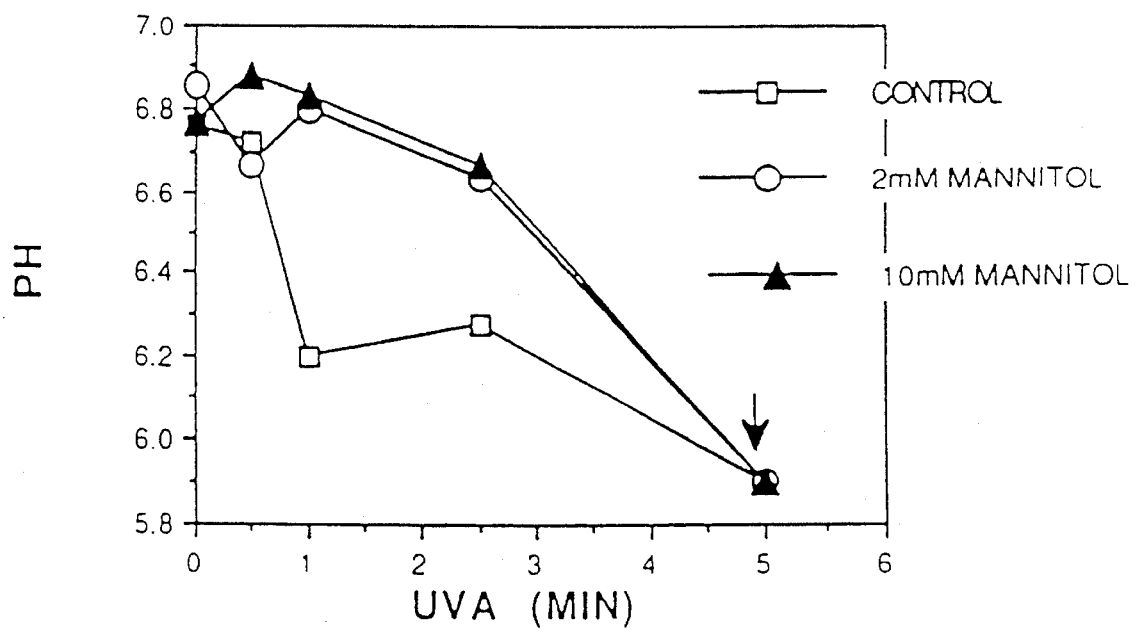
FIG. 9 is a graph showing pH results following treatment and platelet storage.

The remaining amount from the original 50 ml solution was divided into 6 minibags. The minibags were then irradiated (0.5, 1.0, 2.5, 5.0 or 10 minutes as needed) and stored. Platelet function was then followed over time. FIG. 9 is a graph showing pH results, FIG. 10 is a graph showing aggregation results, and FIG. 11 is a graph showing ATP results.

Figure 10:
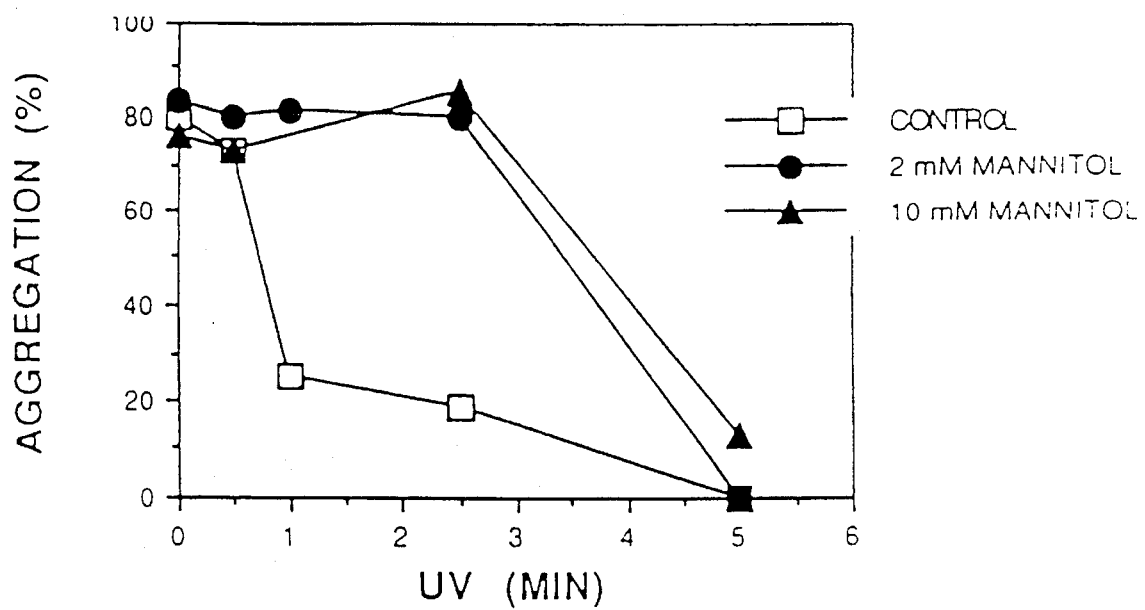
FIG. 10 is a graph showing aggregation results following treatment and platelet storage.
Figure 11:
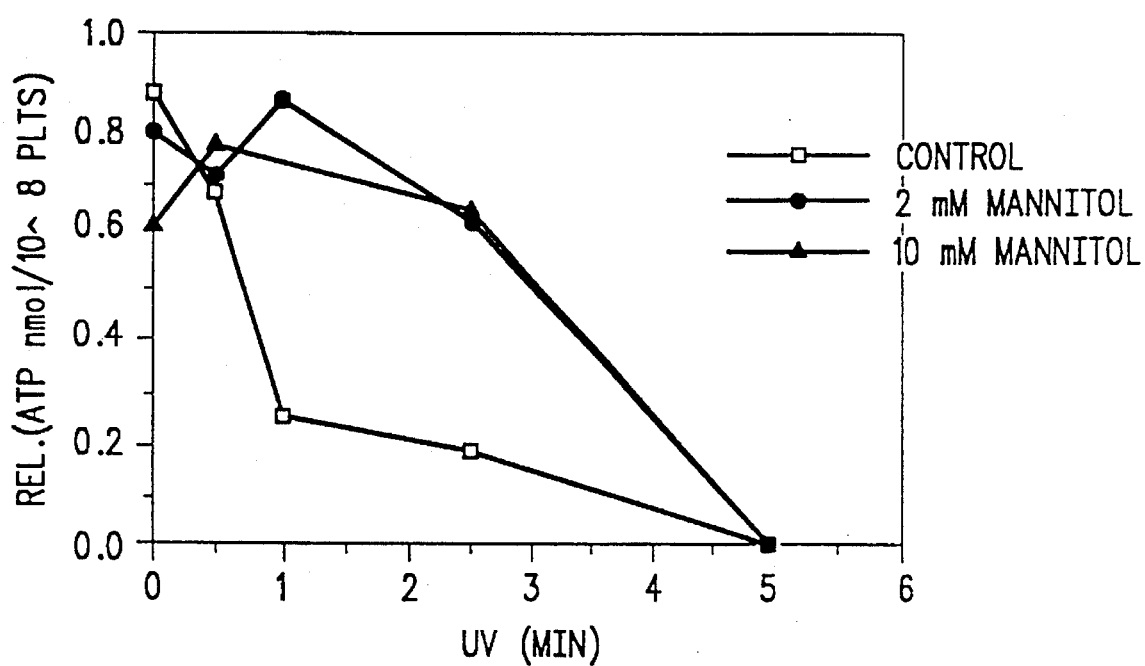
FIG. 11 is a graph showing ATP results following treatment and platelet storage.

FIG. 9, 10, and 11 indicate that extensive damage were obtained by one minute UVA irradiation on platelets resuspended in plasmalyte stored for 4 days. However, 2 and 10 mM mannitol protected platelets during a 2.5 minute UVA irradiation. Clearly, mannitol is helpful in synthetic media to preserve platelet function following irradiation.

We claim:

1. A method of inactivating bacteria in blood preparations, comprising:
    a) providing, in any order, i) 8-methoxypsoralen; ii) photoactivating means for photoactivating 8-methoxypsoralen; and iii) a platelet preparation suspected of being contaminated with bacteria in a synthetic media;
    b) adding said 8-methoxypsoralen to said platelet preparation at a final concentration of between approximately 3 and 30 ug/ml; and
    c) photoactivating said 8-methoxypsoralen, so that said 8-methoxypsoralen binds covalently to the nucleic acid of a portion of said bacteria, without causing significant damage to said platelet preparation.

2. The method of claim 1, wherein said platelet preparation is selected from the group consisting of platelet rich plasma and platelet concentrate.

3. The method of claim 1, wherein said photoactivating means comprises a photoactivation device capable of emitting a spectrum of electromagnetic radiation comprising wavelengths between 180 nm and 400 nm, and having an intensity flux greater than approximately 1 mW/cm$^2$.

4. The method of claim 3, wherein said intensity flux is between 1 and 15 mW/cm$^2$.

5. The method of claim 4, wherein said platelet preparation is exposed to said intensity flux for between one second and ten minutes.

6. The method of claim 5, wherein said platelet preparation is exposed to said intensity flux for approximately five minutes.

7. The method of claim 1, wherein said synthetic media contains mannitol.

8. A method of treating blood preparations intended for in vivo use, comprising:
    a) providing, in any order, i) an aqueous synthetic media containing 8-methoxypsoralen; ii) photoactivating means for photoactivating said 8-methoxypsoralen; iii) a blood preparation, comprising platelets suspected of being contaminated with bacteria;
    b) adding said synthetic media containing said 8-methoxypsoralen to said blood preparation; and
    c) photoactivating said 8-methoxypsoralen with a spectrum of electromagnetic radiation, so that said 8-methoxypsoralen binds covalently to the nucleic acid of a portion of said bacteria, without causing significant activation of said platelets.

9. The method of claim 8, wherein said photoactivating means comprises filters providing wavelength cutoffs at 320 nm, below which no irradiation is transmitted, and at 360 nm, above which no irradiation is transmitted.

10. The method of claim 8, wherein said photoactivating means is capable of emitting radiation having an intensity flux between 1 and 15 mW/cm$^2$.

11. The method of claim 10, wherein said blood preparation is exposed to said intensity flux for between 1 second and 10 minutes.

12. The method of claim 8, wherein said synthetic media contains mannitol.

13. A composition having anti-microbial properties, comprising a blood preparation in a synthetic media comprising 8-methoxypsoralen at a concentration between approximately 3 μg/ml and 30 ug/ml and mannitol at a concentration of approximately 10 mM.

14. The composition of claim 13, wherein said blood preparation comprises platelets.

15. A method of inactivating bacteria in blood preparations, comprising:
   a) providing, in any order, i) an aqueous synthetic media comprising 8-methoxypsoralen; ii) photoactivating means for photoactivating said 8-methoxypsoralen; and iii) a blood preparation, comprising platelets suspected of being contaminated with bacteria;
   b) adding said synthetic media to said blood preparation at a final concentration of 8-methoxypsoralen of between approximately 3 and 30 ug/ml; and
   c) photoactivating said 8-methoxypsoralen, without limiting the concentration of molecular oxygen, so that said 8-methoxypsoralen binds covalently to the nucleic acid of a portion of said bacteria.

16. The method of claim 15, wherein said blood preparation comprises platelet concentrate.

17. The method of claim 15, wherein after said photoactivating of step (c), said blood preparation is stored at room temperature prior to administration in vivo.

18. The method of claim 15, wherein said photoactivating means comprises a photoactivation device capable of emitting a spectrum of electromagnetic radiation comprising wavelengths between 180 nm and 400 nm, and having an intensity flux greater than approximately 1 mW/cm$^2$.

19. The method of claim 18, wherein said intensity flux is between 1 and 15 mW/cm$^2$.

20. The method of claim 19, wherein said blood preparation is exposed to said intensity flux for between one second and ten minutes.

* * * * *